(12) United States Patent
Kingsley

(10) Patent No.: US 8,993,229 B1
(45) Date of Patent: Mar. 31, 2015

(54) METHOD FOR DETECTING AND DISTINGUISHING INFECTIOUS NOROVIRUS FROM INACTIVATED NOROVIRUS

(75) Inventor: David H. Kingsley, Magnolia, DE (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 136 days.

(21) Appl. No.: 13/597,805

(22) Filed: Aug. 29, 2012

Related U.S. Application Data

(60) Provisional application No. 61/530,750, filed on Sep. 2, 2011.

(51) Int. Cl.
*C12Q 1/70* (2006.01)
*C12Q 1/68* (2006.01)

(52) U.S. Cl.
CPC .................................... *C12Q 1/701* (2013.01)
USPC ............... 435/5; 435/6.1; 435/91.2; 435/236; 435/239

(58) Field of Classification Search
CPC ................ C07K 14/005; C07K 16/10; G01N 33/56983; G01N 2333/08
See application file for complete search history.

(56) References Cited

PUBLICATIONS

Tian et al. Two-log increase in sensitivity for detection of norovirus in complex samples by concentration with porcine gastric mucin conjugated to magnetic beads. Appl Environ Microbiol. Jul. 2008;74(14):4271-6.*
Nuanualsuwan and Cliver. Capsid functions of inactivated human picornaviruses and feline calicivirus. Appl Environ Microbiol. Jan. 2003;69(1):350-7.*
Nuanualsuwan S, Cliver Do. Pretreatment to avoid positive RT-PCR results with inactivated viruses. J Virol Methods. Jul. 2002;104(2):217-25.*
Stals, A., et al. "Multiplex real-time RT-PCR for simultaneous detection of GI/GII noroviruses and murine norovirus1" 2009 Journal of Virological Methods 161:247-253.
Tian, P., M. Brandi and R. Mandrell, "Porcine gastric mucin binds to recombinant norovirus particles and competitively inhibits their binding to histo-blood group antigens and Caco-2 cells" 2005 Letters in Applied Microbiology 41:315-320.
Tian, P., et al. "Specifity and kinetics of norovirus binding to magnetic bead-conjugated histo-blood group antigens" 2010 Journal of Applied Microbiology 109:1753-1762.
Kingsley, David H. et al., "Inactivation of human norovirus using chemical sanitizers", (2014) International Journal of Food Microbiology 171:94-99.

* cited by examiner

*Primary Examiner* — Michelle S Horning
(74) *Attorney, Agent, or Firm* — David L. Marks; John D. Fado; Lesley Shaw

(57) ABSTRACT

A method for extracting and distinguishing infectious norovirus from inactive norovirus using a solid support conjugated with a glycoprotein moiety capable of binding infectious norovirus wherein the presence of infectious norovirus is determined using RT-PCR after elution of the infectious norovirus from the solid support.

15 Claims, 3 Drawing Sheets

Figure 1:
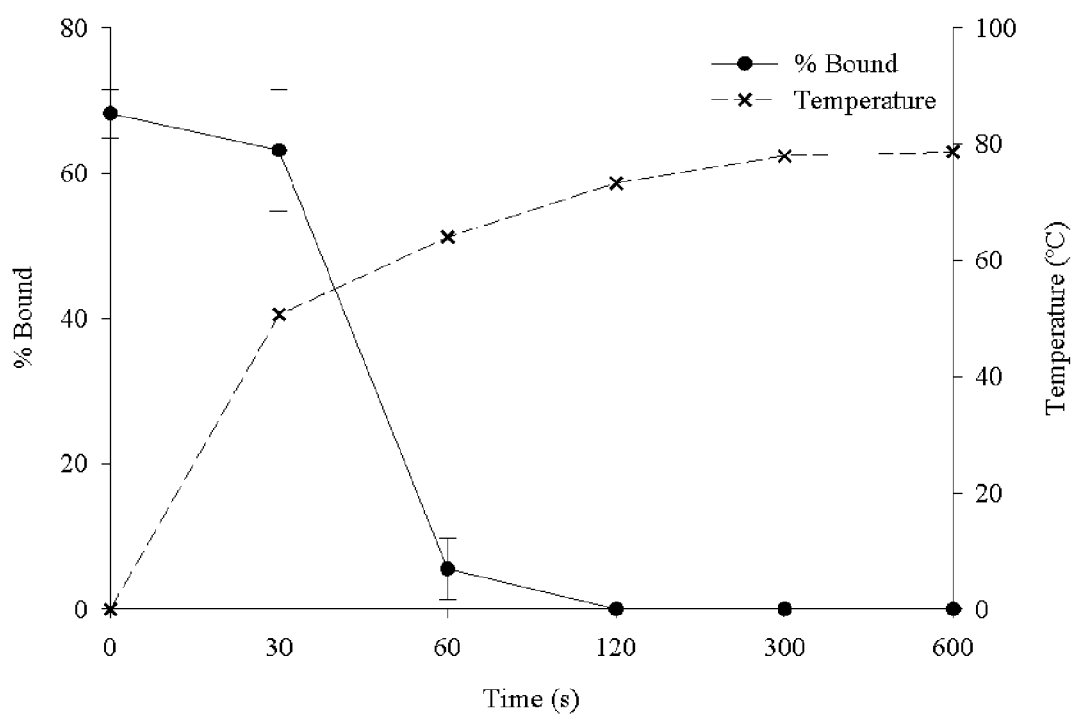

METHOD FOR DETECTING AND DISTINGUISHING INFECTIOUS NOROVIRUS FROM INACTIVATED NOROVIRUS

RELATED APPLICATIONS

This application is claims priority to U.S. Provisional Patent Application Ser. No. 61/530,750 filed Sep. 2, 2011 the contents of which are incorporated herein by reference in their entirety.

BACKGROUND OF THE INVENTION

1. Field of the Invention

This invention relates to a method for preferentially extracting and distinguishing infectious norovirus from inactivated norovirus.

2. Description of the Related Art

Human norovirus is the most frequent cause of foodborne illness in the United States (Anon, Morbidity and Mortality Weekly Report, 59:973-979, 2010), and is spread by consumption of contaminated food or water. Noroviruses, previously called Norwalk-like viruses (NLV), are small, round viruses within the calicivirus family and are important viral pathogens that cause acute gastroenteritis, the second most common illness in the United States. Norovirus illness is normally a mild to moderate illness that develops 1-2 days after infection by person-to-person transmission, surface contamination, or by contaminated food or water and the illness lasts for 24 to 60 hours. Symptoms include nausea, vomiting, diarrhea, abdominal pain, and upon occasion headache and low fever. Severe illness, although uncommon, may require hospitalization. Particularly large epidemic outbreaks of illness have occurred following consumption of contaminated water or uncooked foods, such as salads or sliced deli meats and shellfish, such as clams, cockles, and oysters.

Norovirus have been refractory to reliable propagation in vitro (Duizer et al., Journal of General Virology, 85:79-87, 2004) and there are no practical in vivo assays. Consequently, most methods for detection of norovirus contamination in foods utilize molecular methods such as RT-PCR, targeting the viral RNA genome. While primer specificity has improved dramatically in recent years, and RT-PCR methods are now quite sensitive, these techniques have drawbacks. First, successful RT-PCR requires a relatively pure RNA template, free of molecular amplification inhibitors, necessitating the use of sophisticated biochemical extraction techniques. Furthermore, traditional RT-PCR cannot distinguish between RNA derived from an infectious virus or from an inactivated virus (Richards, J. Food Prot, 62:691-697, 1999). While chemically-altered or highly fragmented RNA may not be successfully amplified and ruptured virus particles leave viral RNA vulnerable to rapid environmental degradation, intact virus particles inactivated as a consequence of damage to capsid or other proteins will contain intact RNA despite being unable to initiate an infection in vivo. Essentially, this creates the potential of a false positive test where the detected virus is not a threat to public health.

For norovirus, it is known that the RNA isolated from virions is sufficient to initiate replication of the virus (Guix et al., J. Virol., 81:12238-12248, 2007). Therefore, inactivation mechanisms that target virus proteins must either perturb or rupture the virus capsid, or alter other structural proteins sufficiently to disrupt the early phases of the viral life cycle before release of viral RNA into the cytosol of the infected cell such as for example, attachment, penetration, or uncoating phases of infection.

Norovirus are known to bind to histo-blood group antigens (HBGAs) on the surface of human cells with different norovirus strains recognizing specific variable antigens expressed by subsets of the human population, which potentially explains why some individuals are susceptible to certain strains and resistant to others (Cao et al., J. Virol., 81:5949-5957, 2007; Donaldson et al., Immunol. Rev., 225:190-211, 2008; Tan and Jiang, Trends Microbiol., 13:285-293, 2005). In addition to demonstrating that histo-blood group antigens can be used to concentrate human norovirus, Tian et al. (J. Appl. Microbiol., 109:1753-1762, 2010) demonstrated that recombinant norovirus-like particles readily bind to the surface of swine duodenum (Tian et al., Res. Vet. Sci., 83:410-418, 2007). Subsequently, Tian et al (Appl. Environ. Microbiol., 74:4271-4276, 2008) demonstrated that when porcine gastric mucin was coupled to magnetic beads (PGM-MB), these beads could be used to expediently extract different strains of norovirus from foods, binding 100% of the GI and 85% of the GII norovirus strains tested.

Virus inactivation methods, which are known to substantially target capsid proteins, include thermal methods such as pasteurization, ultraviolet (UV) light inactivation, high pressure processing (HPP) and chlorination. Nuanualsuwan and Cliver (J. Virol. Methods, 104:217-225, 2002) used protein kinase K and RNase A applied after inactivation by chlorine, ultraviolet light, or 72° C. heat treatments to destroy the inactivated virion and the genomic RNA of poliovirus (PV), hepatitis A virus (HAV), and feline calcivirus. This acquired sensitivity to proteinase K infers alteration of the protein capsid structure, resulting in cleavage of capsid proteins, destruction of capsid integrity by proteinase, and subsequent destruction of the virus genome by RNase A. On this basis, it was suggested by the reference that this treatment could potentially be used to avoid positive RT-PCR results from the presence of inactivated viruses. It was also noted that for thermal and UV inactivation, or hypochlorite treatments of FCV, HAV, and PV, loss of infectivity was usually accompanied by the loss of virus attachment to its homologous cellular receptor (Nuanualsuwan and Cliver, 2002, supra; Appl. Environ. Microbiol, 69:350-357, 2003). More recently, Parshionikar et al. (Appl. Environ. Microbiol., 76:4318-4326, 2010) reported that 72° C. treated norovirus is rendered non-detectable by RT-PCR via reaction and modification of encapsulated RNA with propidium monoazide.

Given the relative difficulties of assaying for inactivation of human norovirus, there is a paucity of data confirming inactivation conditions for these virus strains. Conformational stability studies with recombinantly-expressed norovirus-like particles (VLPs), which are in essence empty norovirus capsids, demonstrated alterations of protein structure at temperatures above 60° C. (Ausar et al., J. Biol. Chem., 281: 19478-19488, 2006). Using plaque assay, temperature inactivation at 60° C. or higher was observed for the genetically-related research surrogate, murine norovirus (MNV; Baert et al., Appl. Environ. Microbiol., 74:543-546, 2008). High pressure processing, another protein-targeting treatment at 6° C. is capable of inactivating at least 4-$\log_{10}$ of GI.1 Norwalk strain (Leon et al, Appl. Environ. Microbiol. 77:5476-5482, 2011). Also, it has been demonstrated that high pressure-treated MNV becomes deficient for binding to the surface of its host cells (Tang et al., Int. J. Food Microbiol., 137:186-189, 2010). Although the degree to which UV irradiation inactivates norovirus strains has not been determined, UV inactivation studies have shown that a UV dose of 25 mJ/cm$^2$ inactivated 3.6-$\log_{10}$ PFU of MNV (Lee et al., Appl. Environ. Microbiol., 74:2111-2117, 2008).

There remains a need for a method for separating and extracting norovirus virions that are potentially infectious for subsequent RT-PCR analysis. The present invention described below is directed to a method for separating and extracting norovirus virions that are potentially infectious from inactivated strains of norovirus which is different from prior art methods.

SUMMARY OF THE INVENTION

It is therefore an object of the present invention to provide methods for use in extracting and detecting infectious norovirus from a biological sample.

Another object of the present invention is to provide a method to extract infectious norovirus in a biological sample using a solid support conjugated with a glycoprotein moiety which binds a norovirus.

A still further object of the present invention is to provide a method that extracts infectious norovirus from a biological sample using a solid support conjugated with a glycoprotein moiety which binds a norovirus followed by elution from said solid support and RT-PCR detection to determine if infectious norovirus is present in the biological sample.

Another object of the present invention is to provide a method that extracts infectious norovirus from a biological sample using a bead conjugated with a mucin which binds infectious norovirus.

A still further object of the present invention is to provide a method that extracts infectious norovirus from a biological sample using a magnetic bead conjugated with porcine gastric mucin.

Further objects and advantages of the present invention will become apparent from the following description.

BRIEF DESCRIPTION OF THE DRAWINGS

FIG. 1 is a graph showing binding of norovirus to mucin after thermal treatment. The treatment temperature profile (degrees C.) as a function of time (0-600 seconds) is shown. The fraction of quantitative RT-PCR (qRT-PCR)-detectable virus binding to PGM-MB after thermal treatment is expressed as a percentage of the original untreated non-PGM-MB-bound stock. Three experiments were each performed in triplicate (N=3, n=9). Error bars indicate standard error of the means.

FIG. 2 is a graph showing binding of GI.1 norovirus to porcine gastric mucin-magnetic beads after exposure to UV treatment. UV treatment of norovirus with approximately 0-2 $J/cm^2$ was performed followed by analysis of virus binding to PGM-MB. Results are shown as average genomic copies/0 detected by qRT-PCR. Black bars represent total norovirus RNA detected after UV treatments prior to interaction with PGM-MBs. Gray bars represent average detected genomic copies/0 of non-binding norovirus after exposure to UV-treated norovirus to PGM-MBs. Checkered bars represent average norovirus bound to PGM-MB after UV treatment. Experiments were performed in triplicate (N=3, n=9). Error bars indicate standard error of the means. Comparing total, bound and unbound groups separately across the five different UV levels, letters indicate statistically significant differences ($p \leq 0.05$ level) when no letter is common (a,b,c,d) among individual total (i.e. black bars only), unbound (i.e. gray bars only) or bound samples (i.e. checkered bars only).

FIG. 3 is a graph showing binding of pressure-inactivated GI.1 norovirus to porcine gastric mucin-magnetic beads. Pressure treatment of virus (0-600 MPa) was performed at approximately 5° C. followed by RNase treatment and binding of the virus to PGM-MBs. Open circles represent qRT-PCR-detected norovirus RNA prior to bead binding. Black circles represent total qRT-PCR-detected after binding and subsequent elution from mucin beads. Triangles represent the amount of norovirus observed to be unbound after HPP treatments. The experiment was performed in triplicate (N=3; n=9). Error bars indicate standard error of the means.

DETAILED DESCRIPTION OF THE INVENTION

The ability to extract and distinguish infectious norovirus from inactivated norovirus will allow detection of infectious virus in biological samples. Currently, methods to recover and detect norovirus in food need to be adapted for each food substance; these have been only rarely used, with the exception of assays to detect virus in shellfish. Drinking water can be tested for noroviruses by using RT-PCR when large (10-100 L) volumes of water are processed through specially designed filters. RT-PCR by itself cannot distinguish RNA derived from an infectious strain of norovirus, from an inactivated virus. While, chemically-altered or highly-fragmented RNA may not be successfully amplified and ruptured virus particles leave viral RNA vulnerable to rapid environmental degradation, intact virus particles inactivated as a consequence of damage to the capsid, or other proteins, will contain intact RNA despite being unable to initiate an infection in vivo. The present invention allows for the extraction and discrimination of infectious norovirus using a solid support conjugated with a glycoprotein moiety which binds an infectious norovirus followed by elution of said infectious virus and confirmation of the presence of infectious norovirus by RT-PCR using, for example, norovirus GI primers and Taqman probe sets described by Stals et al. (Journal of Virological Methods, 161:247-253, 2009; herein incorporated by reference in its entirety). The use of any RT-PCR method for norovirus detection is well within the ordinary skill in the art.

The method of the present invention can be used to test for the presence of infectious norovirus in food products following pasteurization cycles, cooking, high pressure treatment, UV treatments, etc. The method could also be used to establish treatments needed for sewage to inactivate norovirus since water reclamation provides much needed water for farms.

The method of the present invention can use any solid support conjugated with a glycoprotein moiety which binds a norovirus. For purposes of the present invention a solid support refers to any surface that is transferable from solution to solution. The term includes, for example, beads, membranes, microtiter wells, strings, plastic strips, or any surface onto which a norovirus can be immobilized.

As used herein, bead encompasses any type of solid or hollow sphere, ball, bearing, cylinder, or other similar configuration composed of plastic, ceramic, metal, or polymeric material onto which a glycoprotein moiety that mimics a norovirus receptor can be covalently immobilized. As such the term also includes nylon string or strings.

For purposes of the present invention, the glycoprotein moiety which mimics a norovirus receptor, includes, for example, a mucin.

The method of the present invention is exemplified using magnet beads conjugated with porcine gastric mucin (PGM-MBs) and an RT-PCR method as described by Stal et al. (2009). The magnetic beads are prepared using the method of Tian et al. (2007) as follows: MagnaBind carboxyl-derivatized beads (Pierce, Rockford, Ill.) are washed about 3× in approximately 1 ml PBS using a magnet to separate the beads. Any type of magnet bead, or other solid matrix, capable of conjugation with porcine gastric mucin is useful in the present invention. Mucin from porcine stomach, type III (Sigma, St. Louis, Mo.) (10 mg/ml in conjugation buffer containing approximately 0.1 M 2-(4-morpholino)-ethane sulfonic acid with approximately 0.9% NaCl, pH 4.7, is added to the washed beads. A cross linker, 1-ethyl-3-[3-dimethylaminopropyl]carbodiimide hydrochloride (approximately 10 mg/ml) in conjugation buffer is added to the porcine mucin bead mixture and incubated from approximately 30 minutes at about 20-25° C. on a LabQuake shaker rotisserie (Thermo Scientific, Waltham, Mass.) rotating at approximately 8 rpm. A magnetic bead attractor (Stratogene Inc., La Jolla, Calif.) is used to separate porcine mucin-conjugated beads from the solution. The beads are then washed about 3× in approximately 1 ml PBS, resuspended in approximately 1 ml PBS containing approximately 0.05% sodium azide (Sigma) and stored at about 4° C.

Approximately 100 µl of a sample suspected of having infectious norovirus is diluted to approximately 1 ml with phosphate buffered saline (PBS) containing approximately 10 U/ml of RNase inhibitor. Approximately 950 µl of this diluted sample containing an RNase inhibitor is mixed with 50 µl of the PGM-MB preparation and mixed. The sample containing PGM-MB is incubated for approximately 30 minutes at about 20-25° C. on a shaker rotisserie rotating at approximately 8 rpm. Following the incubation period, a magnetic bead attractor is used to separate the beads from the sample solution. The beads are then washed about 3× each with approximately 1 ml of PBS and resuspended in approximately 1 ml of PBS containing approximately 0.05% sodium azide as a preservative to form a sample for RT-PCR. The sample can be stored at approximately 4° C.

The presence of infectious norovirus is then determined using the PGM-MB treated sample using any RT-PCR technique known in the art for detecting the presence of norovirus.

The following examples are intended only to further illustrate the invention and are not intended to limit the scope of the invention as defined by the claims. Magnet beads, porcine gastric mucin and the RT-PCR method of Stal et al. (200, supra) are used to exemplify the method of the present invention.

EXAMPLE 1

Norovirus stocks were prepared from stool containing GI.1 Norwalk stain of norovirus from patient No. 505A-05 from a volunteer study (Richards et al., Journal of Virological Methods, 116:63-70, 2004) and GII.4 was provided the CDC (Atlanta, Ga.). Stool was diluted approximately 1:10 in DMEM with approximately 10% FBS followed by centrifugation at about 12,000×g for about 20 minutes at approximately 4 degrees C. Diluted stocks were passed through a 0.22 µM filter (Nalgene, Rochester, N.Y.) and approximately 1 ml aliquots were made and stored at about −80° C.

PGM-MBs were prepared as described by Tian et al. (2007, supra; herein incorporated by reference in its entirety). In brief, MagnaBind carboxyl-derivatized beads (Pierce, Rockford, Ill.) were washed about 3× in approximately 1 ml PBS using a magnet to separate the beads. Mucin from porcine stomach, type III (Sigma, St. Louis, Mo.) (10 mg/ml) in conjugation buffer containing approximately 0.1M 2-(4-morpholino)-ethane sulfonic acid with approximately 0.9% NaCl, pH 4.7, was added to the washed beads. A cross linker, 1-ethyl-3-[3-dimethylaminopropyl]carbodiimide hydrochloride (approximately 10 mg/ml) in conjugation buffer is added to the porcine mucin bead mixture and incubated from approximately 30 minutes at about 20-25° C. on a LabQuake shaker rotisserie (Thermo Scientific, Waltham, Mass.) rotating at approximately 8 rpm. A magnetic bead attractor (Stratogene Inc., La Jolla, Calif.) was used to separate procine mucine conjugated beads from the solution. The beads were then washed about 3× in approximately 1 ml PBS, resuspended in approximately 1 ml PBS containing approximately 0.05% sodium azide (Sigma) and stored at about 4° C.

EXAMPLE 2

Norovirus stocks were given thermal, UV, and pressure treatments to inactivate the virus as follows:

For thermal treatments, GI.1 stocks were diluted approximately 10-fold with phosphate-buffered saline (PBS) containing RNase inhibitor (approximately 10 U/ml; Invitrogen, Carlsbad, Calif.). Approximately 1 ml aliquots of GI.1 norovirus stock dilutions were added to 1.5 ml microcentrifuge tubes, placed in a heating block set at about 80° C. for about 0-600 seconds and then immediately stored on ice. The temperature profile was recorded in parallel using a thermometer within a microcentrifuge tube containing approximately 1 ml of PBS. Approximately 100 µl aliquots of heated samples were diluted to approximately 1 ml with PBS containing RNase inhibitor (10 U/ml), and assayed using the PGM-MB binding assay, as will be described below in this example.

For UV treatments, GI.1 stocks were diluted approximately 10-fold in PBS containing RNase inhibitor (10 U/ml). Approximately 1 ml of each sample was placed into 6-35 mm dishes. Lids were removed and samples were exposed to UV at approximately 254 nm with doses ranging from about 0-2 J/cm$^2$ using a Stratalinker 2400 (Stratagene, Santa Clara, Calif.). Approximately 100 µl aliquots of UV-treated samples were diluted to approximately 1 ml with PBS containing RNase inhibitor (10 U/ml) and assayed using the PGM-MB binding assay as described below in this example.

For pressure treatments, approximately 1 ml of GI.1 norovirus stock or GII.4 was transferred into polyester Scotchpack pouches (Kapak 500, Minneapolis, Miss.) with a second pouch sealed around the first pouch. Heat-sealing was performed using an Impulse Food Sealer (American International Electric, Whittier, Calif.; Model MP-8). Pressurization of samples was carried out using a high pressure unit with temperature control (Model Avure PT-1, Avure Technologies, Kent, Wash.) using water as the hydrostatic medium. A circulating water bath surrounded the pressure cell to control temperature. Temperatures for the water bath during pressurization were determined using K-type thermocouples. Pressurization of all GI.1 norovirus samples, ranging from approximately 300-600 MPa, was conducted for about 5 minutes at an initial temperature of approximately 5° C. Pressurization of GII.4 norovirus was performed for about 5 minutes at an initial temperature of about 5° C. at approximately 600 MPa only. The temperature increase during pressure treatment due to adiabatic heating was approximately 2.1 degrees C./100 MPa. The pressure come-up time was approximately 22 MPas/second. The pressure-release was approximately <4 seconds. Pressurization time does not include the pressure come-up release time.

After the treatments of the approximately 1 ml aliquots of norovirus, as described above, approximately 50 µl were removed and stored as an initial starting fraction. Approximately 50 µl of PGM-MBs, prepared as described in Example 1, were then added to the remaining approximately 950 µl of virus stock and incubated for about 30 minutes at about 20-25° C. on a LabQuake shaker rotisserie (Thermo Scientific) at about 8 rpm. A magnetic bead attractor was used to separate the PGM-MBs from treated virus stock in a 1.5 ml microcentrifuge tube. The PGM-MBs were washed approximately 3 times in approximately 1 ml PBS and resuspended in approximately 50 μl PBS containing RNase inhibitor (10 U/ml) (Invitrogen). For initial untreated samples prior to interaction with PGM-MBs, and unbound fractions, representing the supernatant after interaction with PGM-MBs, norovirus RNA was released from the norovirus by placing samples in an approximately 99° C. heat block for about 5 minutes. For bound fraction samples, norovirus RNA was directly eluted from the PGM-MBs after resuspension in PBS with RNase inhibitor by heat-release at approximately 99° C. for about 5 minutes followed by use of a magnetic attractor to separate the PGM-MBs from released qRT-PCR.

The norovirus GI primers and TaqMan probe sets were originally described by Stals et al. (2009) QNIF4(+)CGCTG-GATGCGNTTCCAT (SEQ ID NO.: 1); NIVILCR(−)CCT-TAGACGCCATCATTTAC (SEQ ID NO.: 2); and NVGG1p6-FAM-TGGACAGGAYCGRATCT-BHQ-1(SEQ ID NO.: 3), and were purchased from Integrated DNA Technologies (Coralville, Iowa). Reactions were performed using the OneStep RT-PCR Kit (Qiagen, Valencia, Calif.) in accordance with the manufacturers recommended procedures in approximately 25 μl reaction mixtures with approximately 5 U RNase inhibitor (Invitrogen). Reverse transcription of all viral RNA was performed at about 50° C. for about 30 minutes followed by an about 10-minute Taq activation step at approximately 95° C. followed by about 50 amplification cycles using an about 95° C. approximately 15 second denaturation step and an annealing/extension step at about 60° C. for approximately 60 seconds. Primer and probe concentrations were as previously determined by Stals et al. (2009); GI: approximately 500 nM of primer QNIF4, approximately 900 nM of primer NVILCR, approximately 100 nM of probe NVGG1p. The previously described GI plasmid containing a 100 bp GI sequence, including primer/probe binding sites, was used as a positive control standard (10). Plasmid DNA was purified using the Plasmid Maxi Kit (Qiagen) and absorbance was quantified at about 260 nm with a NanoDrop 2000 Spectrophotometer (Thermo Fisher, Wilmington, Del.). Positive controls for the RT step were produced by extraction of viral RNA from the norovirus using ViralAmp RNA extraction kit (Qiagen), and negative controls containing all of the reagents except template were included with each set of reactions. Real-time PCR assays were performed in a Smart Cycler (Cepheid, Sunnyvale, Calif.). The fluorescence was measured during the annealing/extension step of each cycle. The cycle threshold ($C_t$) was defined as the cycle number at which the fluorescence of each sample crossed the threshold value of 30. Standard curves were generated from plotting the regression of duplicate 10-fold serial dilutions ($10^9$ genomic copies to one genomic copy) of the GI plasmid. The $C_t$ values of the viral RNA were applied to the standard curves for quantitative readouts reported as copy number of pGI.1.

Binding percentages to PGM-MBs were calculated based on the detected amount of genomic RNA equivalents bound to mucin beads divided by the total of bound and unbound genomic RNA equivalents detected for each sample. The data were analyzed using Excel software (Microsoft, Redmond, Wash.). Graphs were made using SigmaPlot 11.0 and statistical analyses were performed using SigmaStat 3.5 (Systat Software, Chicago, Ill.). For UV treatments, analysis of variance and multiple comparisons using the Bonferroni LSD method were performed using Proc GLM of the SAS v. 9.22 software (SAS Institute, Cary, N.C.) after using the logarithmic (base 10) transformation on the number of genomic copies/μl to insure the homogeneity of variance assumption.

In three independent trials, GI.1 norovirus binding to PGM-MBs was determined over a temperature range of approximately 0-80° C. by transferring individual tubes of norovirus from ice (0 degrees C.) to an approximately 80° C. in a heat block. The temperature treatment profile and subsequent results for PGM-MB binding are shown in FIG. 1. Initially, an average of approximately 68% of RT-PCR-detectable norovirus was observed to bind to mucin beads with an average of approximately 32% not associating with beads. After about 60 seconds in the heat block at approximately 64° C., an average of only about 6% binding to PGM-MBs was observed. After approximately 120 seconds at approximately 73° C., binding to PGM-MBs was completely abolished.

Figure 2:
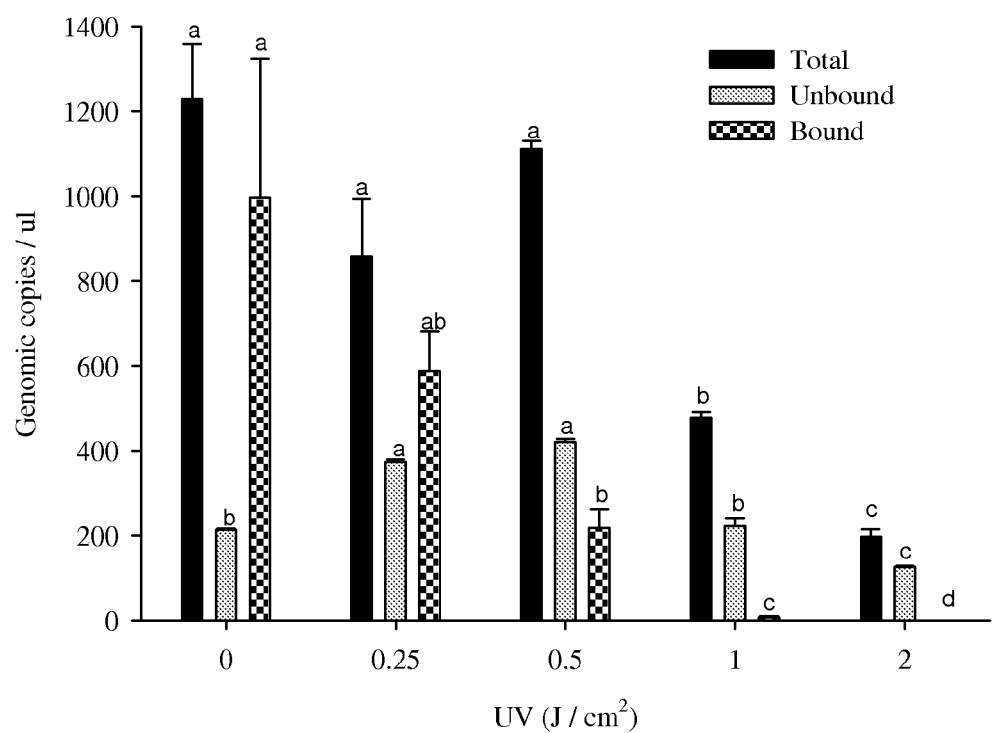

In three independent trials, the ability of GI.1 norovirus to bind to PGM-MBs was assessed after UV treatment. Results are shown in FIG. 2. Initially, the majority, approximately 84%, of non-UV irradiated at approximately 0 J/cm², norovirus bound to the mucin beads. After treatments with approximately 0.5 J/cm², average binding was reduced to approximately 33% of RT-PCR detectable norovirus, while treatments of approximately 1 and 2 J/cm² reduced mean binding to approximately 4% and non-detectable levels, respectively. There was a UV dose-dependent reduction in the RT-PCR detectable genomic copies prior to the PMG-MB binding assay. The overall UV-dose dependent reduction observed was from approximately 1200 genomic copies/0 for non-irradiated norovirus stock to only approximately 200 genomic copies/0 after an approximately 2 J/cm² UV treatment. Presumably, this was due to concomitant damage and chemical modification to the encapsulated RNA by UV, thus reducing the number of RT-PCR amplifiable viral RNA templates. This reduction, however, was less substantial than observed for the effect of UV light on virus binding to PGM-MB, and therefore RNA damage cannot solely account for binding assay results. As compared to non-irradiated samples, approximately 0 J/cm², both the overall amount and proportion of unbound to bound norovirus actually increased with modest UV treatment. For example, approximately 16% of the norovirus detected in non-irradiated samples were bound, while approximately 40% and 67% of detected viruses were unbound after approximately 0.25 and 0.5 J/cm²-treatments respectively.

Recent studies have demonstrated that an approximately 600-MPa treatment is sufficient to inactivate at least 4-$\log_{10}$ of GI.1 norovirus as assessed in volunteers (Leon et al., Appl. Environ. Microbiol. 77:5476-5482). Therefore, HPP-inactivated virus was used to evaluate the ability of pressure-inactivated virus particles to bind to PMG-MB. In initial trials with approximately 5 minute, 600-MPa treatments of GI.1 and GII.4 norovirus at approximately 5° C. performed in triplicate, it was observed that binding of untreated virus to PGM-MBs averaged approximately 71% and 69%, respectively. After pressure-treatment, only approximately 0.3% of GI.1 and approximately 4% of GII.4 virus was observed to bind to PGM-MB (data not shown).

Figure 3:
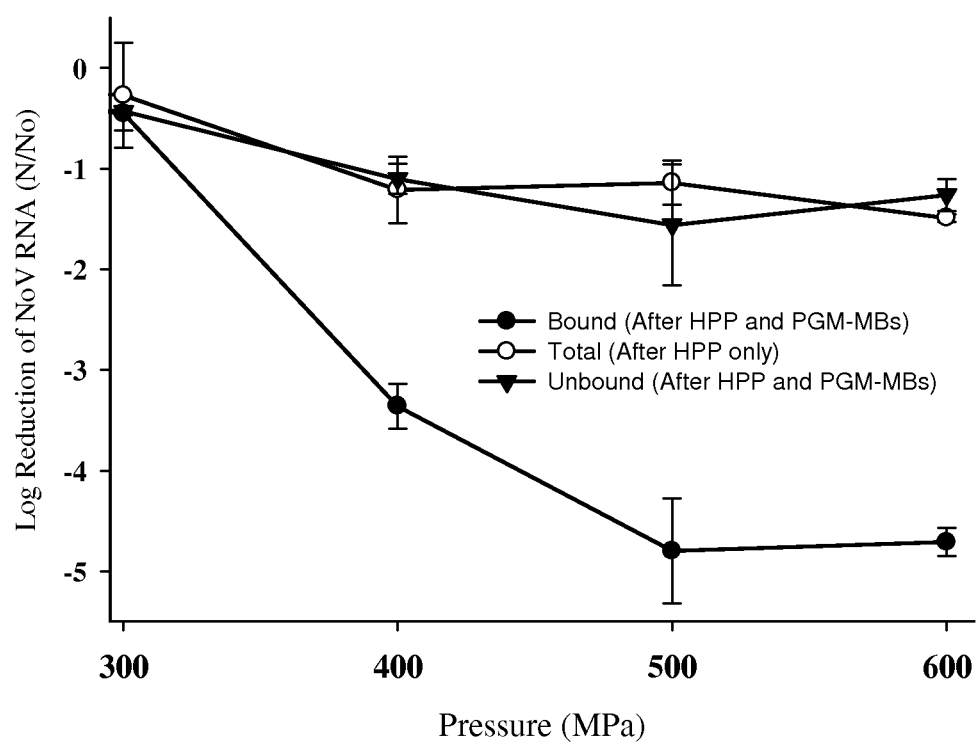

Subsequently, three independent trials were performed by treating norovirus with approximately 300, 400, 500, and 600 MPa for approximately 5 minutes at about 5° C., followed by determination of PGM-MB binding. Initial binding observed was averaged approximately 82%. As shown in FIG. 3, total RT-PCR detectable norovirus RNA is substantially reduced in a pressure-dependent manner by HPP treatment, with about a 5 minute, approximately 600 MPa treatment reducing qRT-PCR detection by approximately 1.5 $\log_{10}$. After binding to PGM-MBs, qRT-PCR detectable norovirus RNA was reduced by ≥4.7 $\log_{10}$ for approximately 500 and 600 MPa-treated norovirus stocks while unbound norovirus (after HPP treatment and PGM-MB) showed a reduction that was similar to the reduction observed for total after HPP samples.

The foregoing detailed description is for the purpose of illustration. Such detail is solely for that purpose and those skilled in the art can make variations without departing from the spirit and scope of the invention.

I claim:

1. A method for extracting and distinguishing infectious norovirus from inactivated norovirus virions comprising:
   (a) obtaining a biological sample suspected of containing infectious norovirus and inactivated norovirus virions,
   (b) mixing a first quantity of said biological sample with a solution containing a solid support conjugated with a glycoprotein moiety capable of binding said infectious norovirus to form a first solution,
   (c) incubating said first solution for a time period effective to allow binding of said infectious norovirus to said solid support conjugated with a glycoprotein moiety capable of binding said infectious norovirus to form a solid substrate bound with infectious norovirus, wherein said inactivated norovirus virions do not bind to said glycoprotein moiety,
   (d) separating said solid substrate bound with infectious norovirus and said biological sample suspected of containing infectious norovirus and inactivated norovirus virions,
   (e) eluting said infectious norovirus RNA from said infectious norovirus bound to said solid substrate to form an infectious norovirus RNA containing solution,
   (f) performing RT-PCR on said infectious norovirus RNA containing solution to obtain a first Ct value,
   (g) separating all norovirus RNA from a second quantity of said biological sample to form a total norovirus RNA solution,
   (h) performing RT-PCR on said total norovirus RNA solution to obtain a second Ct value, and
   (i) comparing said first Ct value and said second Ct value to distinguish between said infectious norovirus and said inactivated norovirus virions in said biological sample.

2. The method of claim 1 wherein said solid support is a bead.

3. The method of claim 2 wherein said bead is a magnetic bead.

4. The method of claim 1 wherein said glycoprotein moiety capable of binding infectious norovirus is a mucin or histo-blood group antigens.

5. The method of claim 4 wherein said mucin is porcine gastric mucin.

6. A method of determining the ability of a potential inactivating agent to inactivate norovirus virions in or on a biological sample containing infectious norovirus comprising
   (a) subjecting a first quantity of said biological sample containing infectious norovirus to said potential inactivating agent to generate a treated biological sample wherein said treated biological sample contains inactivated norovirus virions, infectious norovirus, or a combination thereof;
   (b) mixing said treated biological sample with a solution containing a solid support conjugated with a glycoprotein moiety capable of binding said infectious norovirus to form a solid substrate bound with infectious norovirus, wherein said inactivated norovirus virions do not bind to said glycoprotein moiety;
   (c) separating said solid substrate bound with infectious norovirus and said treated biological sample;
   (d) eluting said infectious norovirus RNA from said infectious norovirus bound to said solid substrate to form an infectious norovirus RNA containing solution;
   (e) performing RT-PCR on said infectious norovirus RNA containing solution to obtain a first Ct value;
   (f) separating all norovirus RNA from a second quantity of said biological sample containing infectious norovirus to form a total norovirus RNA solution;

(g) performing RT-PCR on said total norovirus RNA solution to obtain a second Ct value; and (h) comparing said first Ct value and said second Ct value to determine the ability of said potential inactivating agent to inactivate norovirus virions.

7. The method of claim 6 wherein said potential inactivating agent is selected from the group comprising irradiation, high pressure, temperature, chemical sanitizer, chlorination, enzymes, and a combination thereof.

8. The method of claim 7 wherein said solid support is a bead.

9. The method of claim 8 wherein said bead is a magnetic bead.

10. The method of claim 7 wherein said glycoprotein moiety capable of binding infectious norovirus is a mucin or histo-blood group antigens.

11. The method of claim 10 wherein said mucin is porcine gastric mucin.

12. A method of determining the ability of a potential inactivating protocol to inactivate norovirus in or on a biological sample comprising (a) applying a known quantity of infectious norovirus to said biological sample, wherein said biological sample containing infectious norovirus has a known Ct value when RT-PCR is performed on a quantity of said biological sample containing infectious norovirus;

(b) subjecting a quantity of said biological sample containing infectious norovirus to said potential inactivating protocol to generate a treated biological sample wherein said treated biological sample contains inactivated norovirus virions, infectious norovirus, or a combination thereof;

(c) mixing said treated biological sample with a solution containing a solid support conjugated with a glycoprotein moiety capable of binding said infectious norovirus to form a solid substrate bound with infectious norovirus, wherein said inactivated norovirus virions do not bind to said glycoprotein moiety, and wherein said glycoprotein moiety is histo-blood group antigens or porcine gastric mucin;

(d) separating said solid substrate bound with infectious norovirus and said treated biological sample;

(e) eluting said infectious norovirus RNA from said infectious norovirus bound to said solid substrate to form an infectious norovirus RNA containing solution;

(f) performing RT-PCR on said infectious norovirus RNA containing solution to obtain a first Ct value; and (g) comparing said first Ct value and said known Ct value to determine the ability of said potential inactivating protocol to inactivate norovirus.

13. The method of claim 12 wherein said potential inactivating protocol is selected from the group comprising irradiation, high pressure, high temperature, chemical sanitation, chlorination, enzymatic degradation, and a combination thereof.

14. The method of claim 13 wherein said solid support is a bead.

15. The method of claim 14 wherein said bead is a magnetic bead.

* * * * *

SEQUENCE LISTING

```
<160> NUMBER OF SEQ ID NOS: 3

<210> SEQ ID NO 1
<211> LENGTH: 18
<212> TYPE: DNA
<213> ORGANISM: Norovirus
<220> FEATURE:
<221> NAME/KEY: misc_feature
<222> LOCATION: (12)..(12)
<223> OTHER INFORMATION: n is a, c, g, or t

<400> SEQUENCE: 1
cgctggatgc gnttccat                                                     18

<210> SEQ ID NO 2
<211> LENGTH: 23
<212> TYPE: DNA
<213> ORGANISM: Norovirus

<400> SEQUENCE: 2
ccttagacgc catcatcatt tac                                               23

<210> SEQ ID NO 3
<211> LENGTH: 20
<212> TYPE: DNA
<213> ORGANISM: Norovirus

<400> SEQUENCE: 3
tggacaggag aycgcratct                                                   20
```